United States Patent [19]

Prescott

[11] Patent Number: 5,616,140

[45] Date of Patent: Apr. 1, 1997

[54] METHOD AND APPARATUS FOR THERAPEUTIC LASER TREATMENT

[76] Inventor: Marvin Prescott, 833 Moraga Dr., Suite 15, Los Angeles, Calif. 90049

[21] Appl. No.: 215,263

[22] Filed: Mar. 21, 1994

[51] Int. Cl.[6] ........................................ A61N 5/06
[52] U.S. Cl. ........................... 606/10; 606/9; 606/27; 607/91
[58] Field of Search .................. 606/2, 3, 9–12, 606/27, 28, 13; 128/640; 607/88, 89, 90, 91, 96, 100, 80, 81; 604/291; 219/354, 555; 372/109

[56] References Cited

U.S. PATENT DOCUMENTS

| | | | |
|---|---|---|---|
| 4,676,246 | 6/1987 | Korenga | 607/96 |
| 4,915,108 | 4/1990 | Sun | 607/96 |
| 5,000,752 | 3/1991 | Hoskin et al. | 607/89 |
| 5,259,380 | 11/1993 | Mendes et al. | 606/9 |
| 5,272,716 | 12/1993 | Soltz et al. | 372/109 |
| 5,300,097 | 4/1994 | Lerner et al. | 607/93 |
| 5,358,503 | 10/1994 | Bertwell et al. | 606/9 |

*Primary Examiner*—Angela D. Sykes
*Assistant Examiner*—Michael Peffley
*Attorney, Agent, or Firm*—Graham & James LLP

[57] ABSTRACT

A battery operated, portable laser bandage having one or many lasers or hyper-red light emitting diodes imbedded therein may be worn by a patient and applied to a specific treatment area. The device supplies the patient with a preprogrammed laser therapy regimen. The patient may wear the device for up to a week between visits to a physician. At the end of the prescribed treatment length or at the end of a week, batteries in the device may be changed or recharged and the physician may re-program the device for a different treatment regimen, if desired. The device is small enough to be worn under clothes and does not interfere with the patient's normal activities.

28 Claims, 10 Drawing Sheets

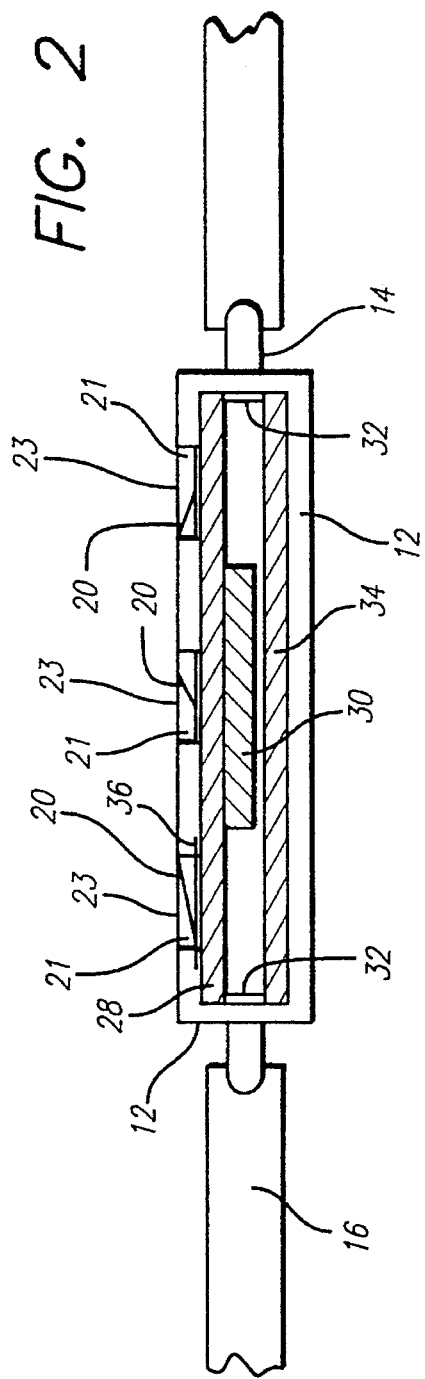
FIG. 2
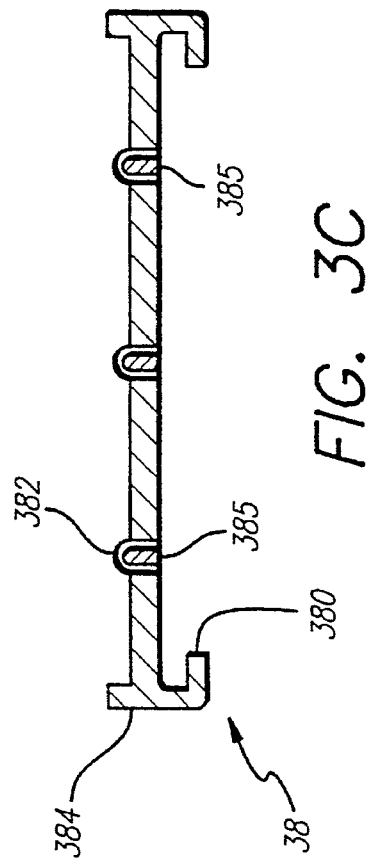
FIG. 3C
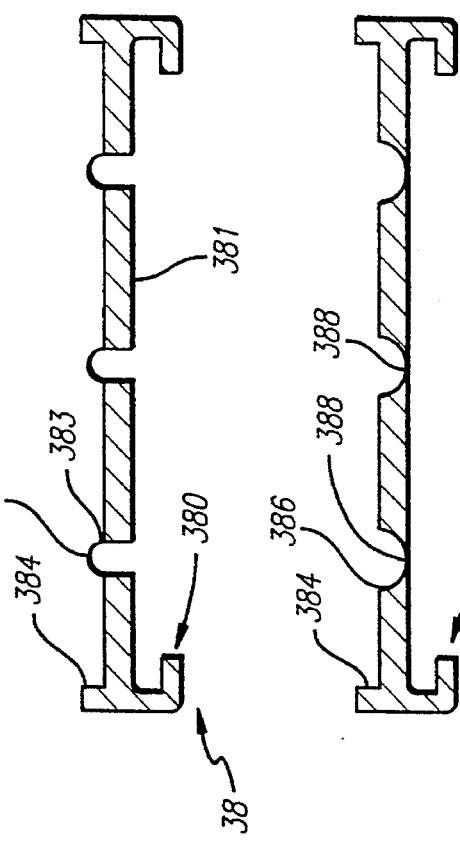
FIG. 3A
FIG. 3B

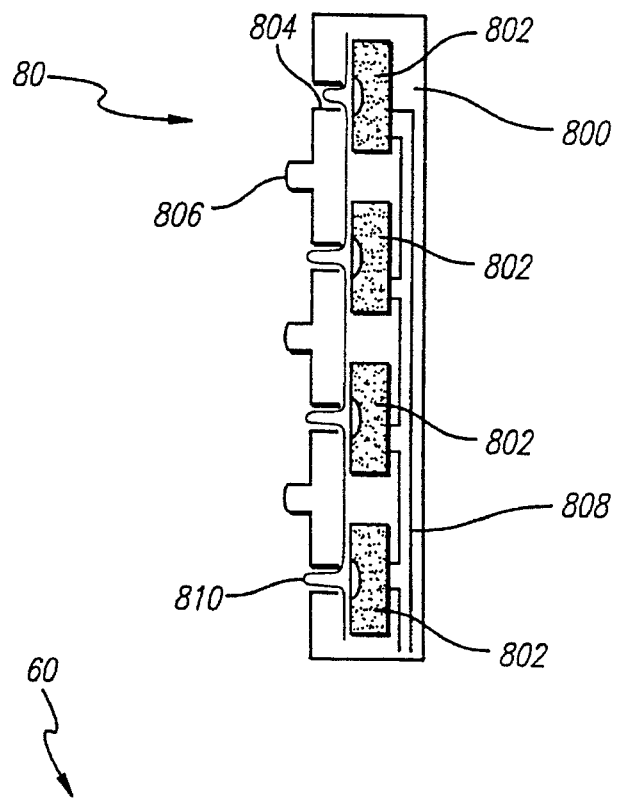
FIG. 8
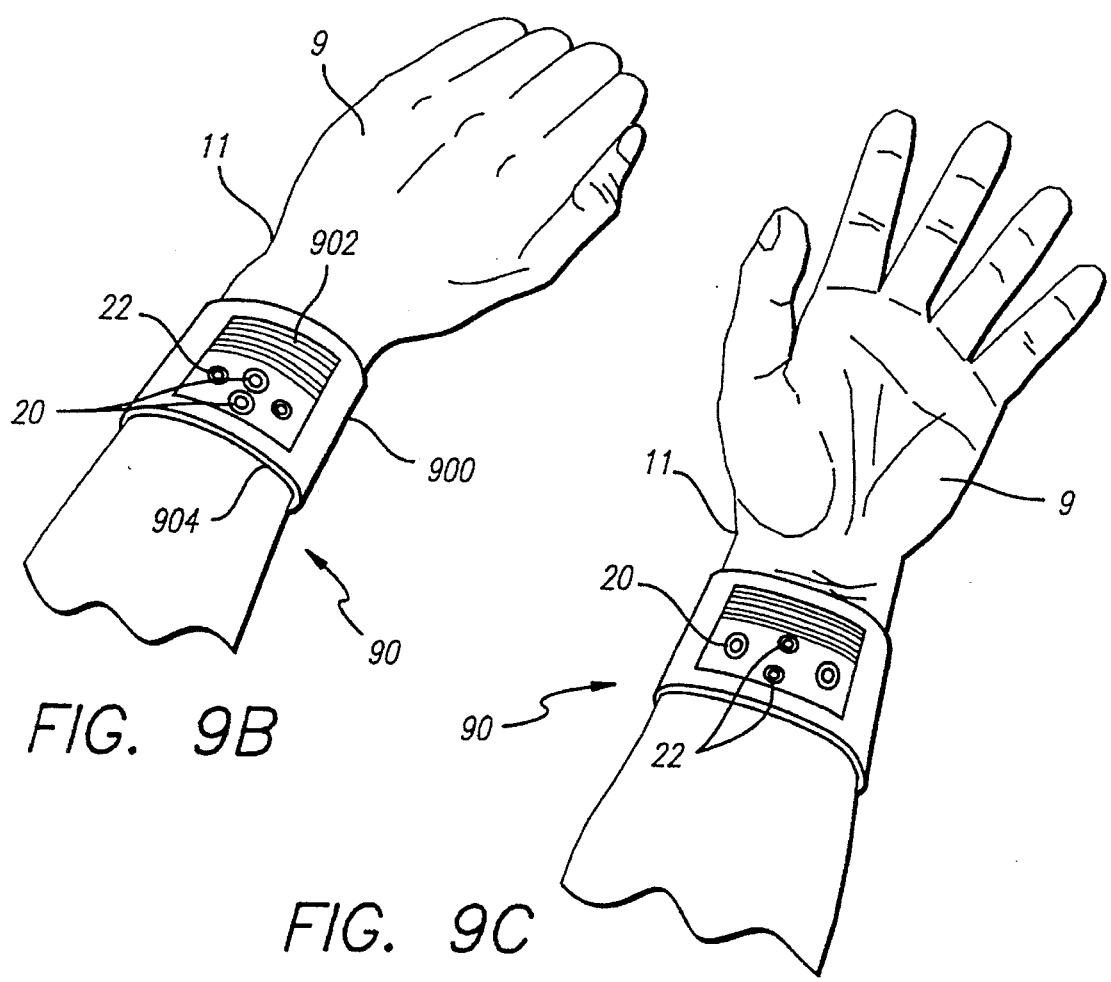
FIG. 9B
FIG. 9C

FIG. 9A
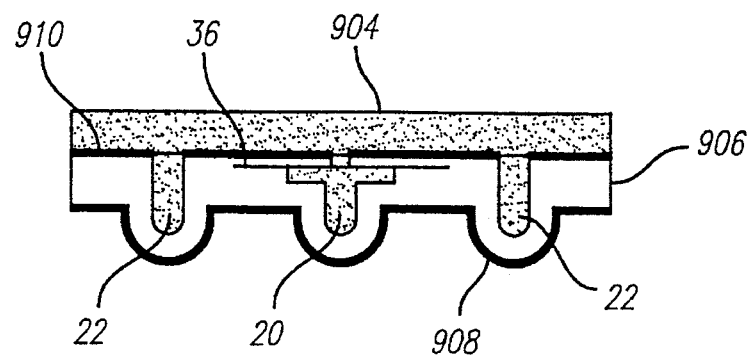
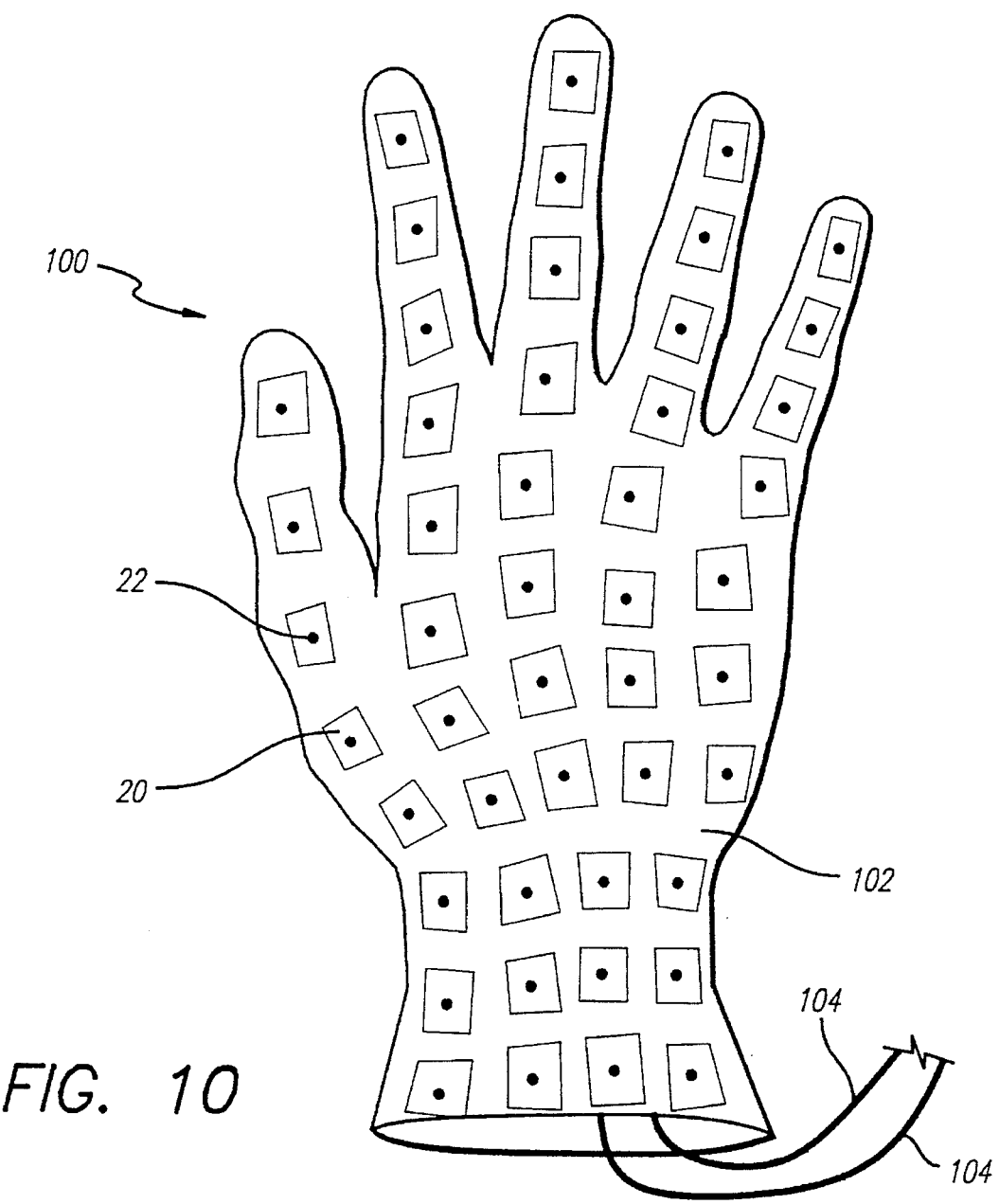
FIG. 10

METHOD AND APPARATUS FOR THERAPEUTIC LASER TREATMENT

FIELD OF THE INVENTION

The present invention is directed to a method and apparatus for applying laser beam energy in the treatment of medical conditions. More particularly, the present invention is directed to a method and apparatus for applying laser beam energy in a medical treatment regimen using a bandage sheet or strip of lasers capable of delivering a concentrated application of laser beam energy to a treatment area in a cost effective and efficient manner.

BACKGROUND OF THE INVENTION

The application of laser beam energy in the treatment of medical conditions is known. Studies have shown that the application of low power laser beam energy on the order of 1 to 100 milliwatts and in varying wavelengths (e.g. 630 nM–904 nM) is effective in the treatment of various medical conditions. In particular, low level laser beam energy has been shown to enhance wound healing and reduce the development of scar tissue after surgical procedures, relieve stiff joints and promote the healing of injured joints, stimulate the body's ability to heal fractures and large contusions as well as enhancing the healing of difficult, slow-to-heal or non-healing decubitus or diabetic ulcers in patients.

Currently, medical and dental applications for low level laser beam energy of varying wavelengths include pain control, wound healing, nerve stimulation, reduction of edema, reduction of inflammation, arthritis, muscle and tendon injuries, and stimulation of the body's neurotransmitter and neurohormone system. In addition, studies by Dima, et al. and Skobelkin published in the Laser Therapy Journal have shown that low doses of incident laser energy in animals modulate the immune response in a cancer affected immune system. Levels of specific immunoglobulins increased for several days post-irradiation compared with un-irradiated controls and immunohistology showed increased activity in cells specifically connected with the immune system and antigen response: T-lymphocytes (including helper T-cells, suppressor T-cells, and killer T-cells); B-lymphocytes, and leukocytes.

One particularly effective use of low level laser beam energy has been in the treatment of uncontrolled bleeding in joint areas, and the related pain associated therewith, in hemophiliac patients. U.S. Pat. No. 5,161,526, issued on Nov. 10, 1992 to Hellwing et al., discusses the application of low level laser beam energy in the treatment of hemophiliac patents. Hellwing, et al. provide test results which show that the application of low level laser beam energy to afflicted joints actually reduced swelling, reduced or eliminated pain and produced a reduction in the size of hematomas in hemophiliac patients. Additional research has shown that the application of laser beam energy of as little as 2.5 milliwatts provides a beneficial effect on a patient undergoing treatment.

Scientific research into the mechanisms of how the body responds to low power laser beam energy suggests that photobiostimulation accelerates the initial phase of wound healing by altering the level of prostaglandins. The laser beam energy additionally increases ATP synthesis by enhancing electron transfer in the inner membrane of the mitochondria, accelerates collagen synthesis by increasing DNA and RNA synthesis, enhances fibroblastic activity and increases the ability of immune cells to ward off invading pathogens by increasing the activity of leukocytes and macrophage cells. In cases of nerve damage, low power laser energy has been shown to stimulate neuronal regeneration. In addition, evidence suggests that the application of low power laser beam energy increases the speed of healing and the tensile strength of damaged tendons and normalizes the repair pattern of lymph vessels and capillaries in a wound site.

Conventional low power (less than 100 milliwatts) laser therapeutic devices generally comprise a hand-held probe with a single laser beam source, or a large, stationary table console with attached probe(s) powered by a conventional fixed power supply. A common laser beam source is a laser diode. Laser diodes are commercially available in varying power and wavelength combinations. Large probes which contain multiple laser diodes affixed to a stand are also known. Such large, multi-beam devices are typically very expensive and require extensive involvement of medical personnel when treating a patient.

For example, in a device such as the large probe containing multiple beam sources discussed above, this device is typically affixed to a stand which has to be focused and controlled by a doctor or ancillary medical personnel. In addition to adding to the cost of the device and the treatment therewith, such a device requires a patient to travel to the location of the laser treatment device in order to obtain the laser therapy. Studies have shown that such treatment typically must be provided on a regular basis (e.g., every few hours or daily) once the treatment is initiated in order to be effective and to produce optimum results. This requires numerous patient visits to the treatment facility or extensive waiting on the part of the patient. As it is common for problems to arise which necessitate a patient missing a visit to the treatment facility, or for a patient to be inconsistent in the times at which appointments are scheduled, the efficiency of the treatment regimen may be lowered or the length of the treatment regimen (i.e., the number of patient visits) may be increased.

In the case of wound healing or tissue healing in general (e.g. bones, tendons, ligaments, skin, nerves), this may result in a less than optimum response by the patient while at the same time increasing the cost of the treatment and the amount of possible scar tissue formation. For patients who are experiencing painful joint injuries, such as arthritic or hemophiliac patients, simply travelling to the facility can cause tremendous physical pain and expose the patient to risk of further injury caused by the travel.

In addition to increasing the financial cost to the patient, a patient may be adversely affected by the number of required visits to the treatment facility in ways which are less tangible. That is, in addition to being away from family members, a patient is generally incapable of working or otherwise being productive while at the treatment facility. The high number of visits interferes with a patient's normal routine and can adversely affect a patient's job performance or home life.

SUMMARY OF THE INVENTION

The present invention is intended to solve the aforementioned problems with prior art laser therapeutic devices while providing a method and apparatus for delivering a laser treatment regimen that is economical, convenient and more efficient than was previously possible. Instead of requiring a doctor or ancillary medical personnel to apply the laser therapy to a patient on a periodic, often irregular schedule, the laser therapeutic device of the present invention allows a doctor to utilize a pre-programmed laser treatment regimen which applies a desired amount of laser beam energy at prescribed time intervals.

In a preferred embodiment of the present invention, a combination of laser beam energy and energy from hyperluminescent ("hyper-red") light emitting diodes may be employed in the treatment regimen. The present invention allows for the application of such treatments in a manner which does not require constant office visits or the constant involvement of the attending physician or ancillary medical personnel.

The present invention solves the problems of the prior art by providing a laser therapeutic device capable of applying laser treatment to a specific area of the patient's body such as a wound site, or to a generalized area of the body such as a knee, ankle, foot, etc., or to the patient's entire body in a systematic, pre-programmed manner to obtain optimum results while decreasing the cost associated with such treatment. The present invention provides for the automatic delivery of the treatment regimen on a schedule which may be pre-programmed by an attending physician or the manufacturer, and which does not require the involvement of medical personnel in the application thereof. The present invention optimizes the results obtainable through laser therapy while eliminating numerous office visits and the costs associated therewith.

Further, the present invention provides an unobtrusive laser treatment apparatus which may be worn by a patient undergoing laser treatment, thereby avoiding interference with the patient's normal activities. More specifically, the device of the present invention may be worn under clothing on a daily basis by the patient, while delivering pre-programmed intervals of laser treatment. Alternatively, the therapeutic device of the present invention may be worn periodically by a patient (e.g., in the evening, while sleeping, etc.) to enhance the benefits of the laser treatment.

By utilizing a pre-programmed laser treatment regimen which delivers laser therapy consistently and at regular intervals, the present invention avoids the problems with the prior art laser treatment devices. By providing a laser therapeutic device which can be worn by the patient, the problems associated with the bulky, expensive laser therapeutic devices of the prior art which required a patient to travel to the doctor's office are eliminated.

These and other advantages of the present invention will become more apparent upon a reading of the detailed description of the preferred embodiments which follows, when considered in conjunction with the FIGURES of which the following is a brief description. It should be clear that the FIGURES are merely illustrative of the inventor's currently preferred embodiments of the present invention, and that the invention is in no way limited to such embodiments. The present invention is best defined by, and solely limited by, the claims appended to this specification.

BRIEF DESCRIPTION OF THE DRAWINGS

FIG. 2 is a cross-sectional side view of the laser therapeutic apparatus shown in FIG. 1.

FIGS. 3A, 3B and 3C are cross-sectional side views of a disposable cap usable with the laser therapeutic apparatus shown in FIG. 1.

FIG. 8 illustrates a partial side view of a sixth embodiment of a laser therapeutic apparatus in accordance with the present invention.

FIGS. 9B and 9C illustrates top and bottom views of a seventh embodiment of a laser therapeutic apparatus in accordance with the present invention.

FIG. 9A is a partial, side cross-sectional view of the laser therapeutic apparatus shown in FIGS. 9B and 9C.

FIG. 10 illustrates an eighth embodiment of a laser therapeutic apparatus in accordance with the present invention.

DETAILED DESCRIPTION OF THE PREFERRED EMBODIMENTS

Figure 1:
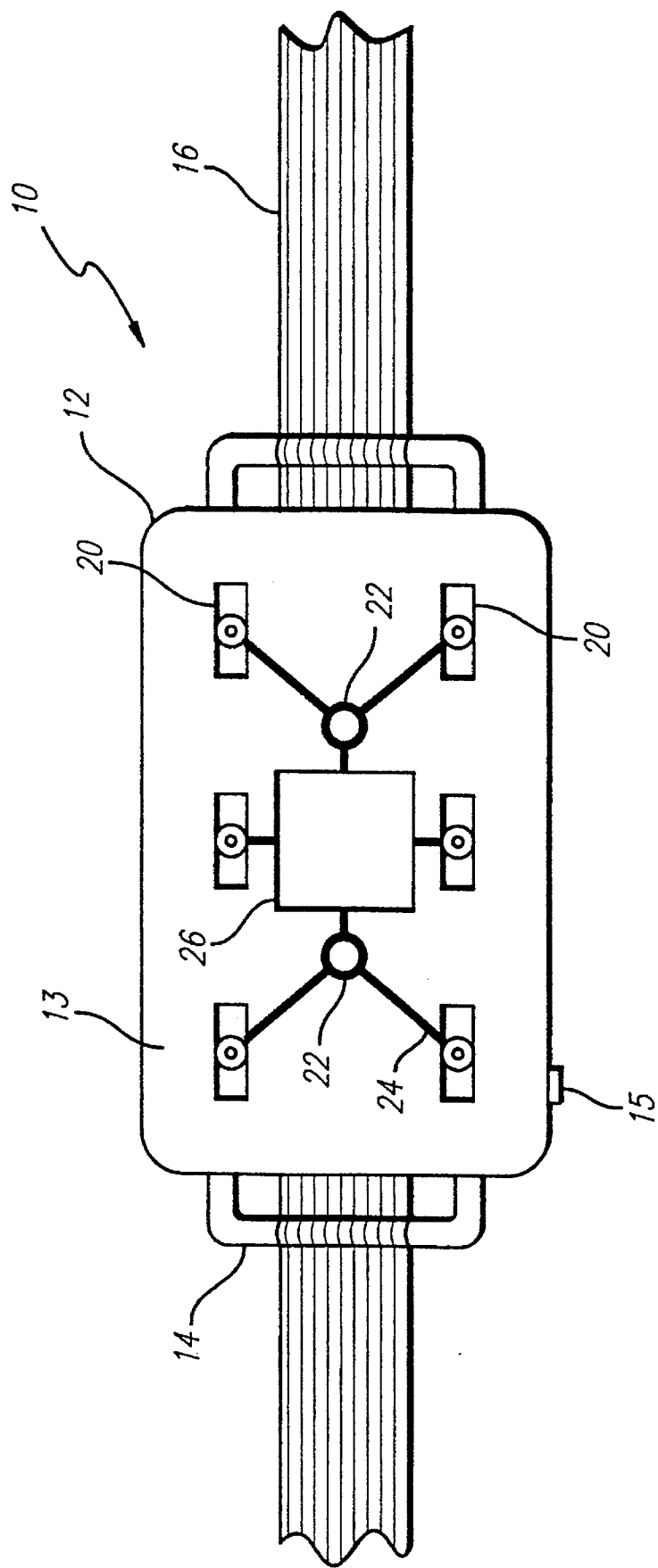
FIG. 1 is a top plan view of a first embodiment of a laser therapeutic apparatus in accordance with the present invention.

FIGS. 1–3C illustrate a first preferred embodiment of the present invention. It should be understood that the following discussion of the presently preferred embodiments is not to be considered in a limiting sense. Rather, it is to be understood that numerous modifications, additions, and/or substitutions can be made to the preferred embodiments without departing from the spirit and scope of the present invention.

A laser therapeutic device 10 in accordance with the first preferred embodiment includes a body or housing 12 having attached thereto a pair of strap hooks 14 for receiving a strap 16 for supporting the device 10. Preferably an assortment of 2.6 milliwatt lasers 20 and hyper-red light emitting diodes 22 are distributed about an area of the surface 13 of the housing 12 and are interconnected by flexible, flat wire connectors 24. The flat wire connectors 24 lead to a central power supply and control circuit 26.

The "housing" 12 may actually be made of molded silicone to which is bonded a flexible printed circuit board 28 and a flexible lithium polymer battery. This structure will be discussed in more detail below.

The lasers 20 are preferably vertical-cavity surface-emitting lasers (or VCSELs) having a nominal power output of 2.6 milliwatts and a wavelength on the order of 600–800 nanometers, with the preferred wavelength being approximately 780 nanometers. The preferred power output of the lasers ranges from 2.6 to 10 milliwatts, with up to 100 milliwatts being possible. However, the inventor has found that 2.6 milliwatts represents a preferred operating level that affords sufficient power for laser treatments and allows for extended battery life.

Vertical cavity surface emitting lasers are known and comprise semiconductor lasers which emit a collimated beam normal to the surface of the semiconductor substrate. The semiconductor typically comprises aluminum arsenide (AlAs) or gallium arsenide (GaAs), or some combination thereof. Each VCSEL has a self contained, high-reflectivity mirror structure forming a cavity to produce the collimated beam. Due to the ability of VCSELs to produce the collimated beam, it is unnecessary to provide additional collimating lenses to focus the beam. While it would be possible to utilize laser diodes in place of the VCSELs in the present invention, the inventor has found that VCSELs represent a preferred laser beam source over conventional laser diodes due to the reduced size and power consumption of the VCSELs. A typical VCSEL may be on the order to 300 micrometers long, have an operational power threshold below 1 milliamp, and consume very little power compared with conventional laser diodes, thus enabling numerous VCSELs to be powered from a single battery source.

In addition, VCSELs have the capability to produce light in the infrared, visible and ultraviolet spectrums, thus allowing for additional applications for the device of the present invention, as will be discussed in more detail below. Accordingly, the VCSEL provides a preferred source of laser beam energy for the present invention. For purposes of the discussion below, it should be clear that where the terms "laser" or "lasers" are used, the preferred embodiment uses VCSELs but conventional laser diodes are also applicable.

The VCSELs are preferably one millimeter in height or less and can be imbedded between layers of silicone or bio-compatible polymer material having a preferable thickness of one millimeter, but which thickness can be varied as desired. Arrays of VCSELs, preferably spaced by one-half inch, can be "sandwiched" between the silicone or polymer material and interconnected with flexible electrical connectors, e.g., flat wires, to form flexible sheets, or bandages, having a total thickness of approximately three millimeters which can be applied to a patient's body and conform to the contours thereof. Preferably, the arrays of VCSELs would be electrically connected in parallel to avoid having a single inoperative VCSEL prevent numerous other VCSELs from operating.

The hyper-luminescent red ("hyper-red") light emitting diodes ("LEDs") emit a light beam having 2000–3000 candle power and a wavelength of approximately 670 nanometers. The hyper-red LEDs may also be arrayed in a manner similar to the VCSELs to form flexible sheets, or bandages for application to a patients body. In the preferred embodiment, the hyper-red LEDs and the VCSELs are arrayed in an alternating fashion (e.g., several VCSELs for every hyper-red LED).

The power supply and control circuit 26, the operation of which may be initiated by means of a single-pole, double-throw or pressure switch 15, provides power and timing control for operation of the lasers and the hyper-red LEDs. The timing control includes initiating the operation of the lasers and the LEDs for a predetermined time period in accordance with a prescribed laser treatment regimen. A control device for performing such a function is known in the art and may comprise a programmable controller having a 24 hour timing function and which initiates operation of the laser diode for a predetermined period of time over the course of the 24 hour period. Preferably the therapeutic device of the present invention is programmed to deliver two-minutes of laser therapy at four hour intervals for five to six days.

Figure 1A:
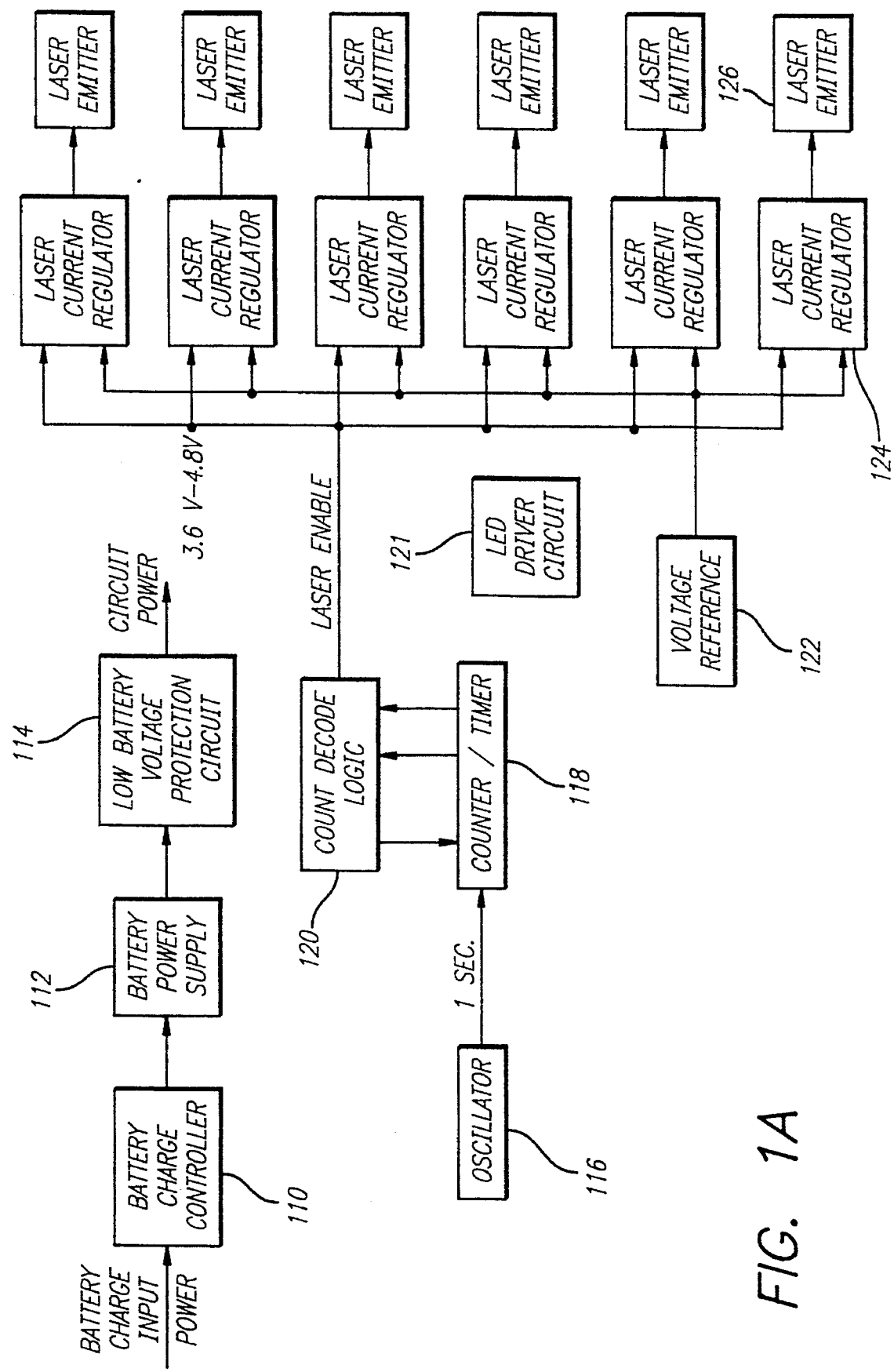
FIG. 1A is a block diagram showing a preferred embodiment of a power supply and control circuit for the laser therapeutic device of FIG. 1.

A preferred embodiment of controller/power supply circuit 30 is shown in FIG. 1A. A battery charge controller 110, which may be connected to an external power source, supplies a battery power supply 112 with a charge when the charge controller 110 is connected to the external source. When an optimum charge level is reached, the charge controller ceases supplying the battery 112 with the charge. Preferably, the battery 112 is capable of maintaining a charge sufficient for one-week of laser therapy, based on a treatment being provided for two minutes every four hours. A low battery voltage protection circuit 114 regulates the power supplied by the battery 112 and provide a voltage output between 3.6 and 4.8 volts. The protection circuit 114 ceases the supply of power if the voltage drops below the threshold level of 3.6 volts to avoid damage to circuit components.

The power supplied by the protection circuit 114 is used to power the circuit components as well as the lasers and hyper-red LEDs. A standard LED driver circuit 121 would be used to drive the hyper-red LEDs 22. This circuit, which is known in the art, would receive power from the circuit power output of the low battery voltage protection circuit 114. An oscillator 116 is provided which supplies pulses at one second intervals to a counter/timer circuit 118. The counter circuit 118 simply counts the pulses while a count decode logic circuit 120 monitors the count.

The count decode logic circuit 120 is a multipurpose logic circuit which may comprise, for example, a PAL (programmable array logic) or a PLA (programmable logic array) that may be programmed to detect certain counts, e.g., 14,400 which would correspond to four hours of time and 120 which would correspond to two minutes of time. Circuit 120 would be capable of maintaining the stored timing program without power being applied thereto. The count decode logic circuit 120 may also comprise a discrete logic circuit formed of standard logic components. While such a circuit would be more cost efficient from low-volume manufacturing perspective, the preferred count decode logic circuit 120 comprises a programmable logic circuit to afford maximum flexibility in operation of the laser therapeutic device of the present invention.

Upon detecting the programmed count, the count decode logic circuit outputs a laser enable pulse which enables laser current regulator circuits 124 which regulate the power to each laser diode 20. The regulator circuits, which are known in the art and which compare the current with a known voltage reference in order to maintain a constant current output, receive a voltage reference input from a voltage reference circuit 122. The voltage reference circuit 122 may comprise an active bandgap zener diode which supplies a constant voltage output (on the order of 1.2 to 1.5 volts) regardless of the voltage of the battery 112. At the same time, the logic circuit 120 provides a RESET pulse to the counter/timer circuit 118 to reset the count, and the counter 118 continues counting the pulses from the oscillator 116.

The laser enable pulse remains active for the programmed length of treatment, e.g. two minutes, or 120 counts in the counter 118. While enabled, the current regulators 124 in the lasers 20 use the input from the voltage reference circuit 122 to provide a predetermined amount of current to produce a beam having, for example, 2.6 milliwatts. The beams are produced by the laser emitters 126. The logic circuit 120 continues to monitor the count in the counter 118 and detects when the count reaches a programmed amount corresponding to the prescribed treatment length (e.g., 120), and then terminates the laser enable signal. At the same time, the logic circuit 120 provides a RESET pulse to reset the count in the counter 118, and the cycle begins again.

The controller/power supply circuit 30 is installed on a single flexible circuit board 28 which may be sufficiently thin (on the order of one millimeter) to be encapsulated by silicone or polymer sheet so as to be formed integral therewith. The control circuit 30 illustrated in FIG. 1A may be made of multiple circuit components which are readily available from electronics suppliers or may be implemented in an application specific integrated circuit (ASIC) to reduce the size and complexity thereof.

Further, it should be understood that while FIG. 1A illustrates a preferred embodiment of a power supply and control circuit 30, any suitable power supply and control circuit may utilized with the present invention provided it meets the constraints imposed by the circuit components such as the VCSELs and LEDs, as well as the desired treatment regimen. Thus, the circuit must maintain a supply voltage of preferably between 3.6 and 4.8 volts and must enable the laser circuitry at the prescribed time and for the prescribed duration (e.g., two minutes every four hours).

Referring to FIG. 2, the partial cross-sectional side view of the laser therapeutic device 10 shown in FIG. 1 reveals a flexible printed circuit board 28 that supports the lasers 20 and/or the hyper-red LEDs 22 being surrounded by a flexible silicone case 12. The flexible printed circuit boards may be made using a flexible, non-conductive material such as Kapton which is available from Dupont. Flexible circuit boards may also be made of Ultem, a flexible, non-conductive material available from GE corporation. The case 12 is provided with openings 21 formed therein to accommodate the light produced by lasers 20. The openings 21 may be provided with clear windows thereover to protect the lasers from dust, oils, dirt, etc. The clear windows 23 are preferably formed of optically clear silicone which is co-molded with the casing 12. However, the windows may also be formed of glass, plastic, or other suitable materials.

The power supply and control circuit 26 preferably includes a three volt, wafer thin, flexible, lithium polymer battery 34 and a programmable controller 30. Alternatively, the battery 34 could be a simple three volt lithium battery or a rechargeable nickel-metal hydride battery. Preferably, the battery can provide sufficient power for a seven day treatment regimen. In the case of the nickel-metal hydride battery, these batteries could be recharged after a five or six day treatment cycle using known methods.

Since the housing 12 may comprise a flexible "sandwich" of silicone bonded to the circuit board 28 and battery 34, support posts 32 may optionally be used to provide rigidity to the housing 12, as well as to provide spacing to accommodate the internal components such as the lasers, hyper-red LEDs and the programmable controller.

The inventor of the instant application has found that when laser diodes are used as the lasers 20, the diodes may generate excessive, and possible damaging, heat when operating. Accordingly, the present invention provides for heat sinks 36 to be associated with each laser diode (only one heat sink 36 is illustrated. The heat sinks are preferably formed of copper and are used to disburse the excess heat produced by the laser diodes into the surrounding housing material. The heat sinks 36 also lend added structural integrity to the locations of the laser diodes. However, if the preferred laser diodes (VCSELs) are utilized, the heat sinks may be omitted as the VCSELs do not generate the heat found in conventional laser diodes.

A pre-formed, sterilized, disposable resilient cover 38 is used to encase the device 10. The cover has a plurality of openings formed therein to accommodate the laser beams produced by the lasers and the light produced by the hyper-red light emitting diodes 22. The cover, which is preferably formed of the same silicone or bio-compatible polymer as used in the housing 12, is held in place by a friction fit over the housing 12. With the cover in place, the entire structure of the device has a thickness of +/– six millimeters.

In addition to protecting the therapeutic device 10 and providing a cushioning agent in the application of the device 10 to the patient's body, the cover 38 also serves an additional function. The pre-sterilized cover 38 serves as a disposable cover which may be applied over those portions of the instrument which contact the patient's body. The disposable/sterilized nature of this portion of the instrument assists in preventing the spread of bacteria and insuring that only sterile surfaces contact the patient's body and the treatment area.

Referring to more detail of FIGS. 3A–3C, the disposable cover 38 may be made in different configurations. FIG. 3A illustrates a disposable cover 38 having a preformed retaining member 380 which partially surrounds the back surface of the housing 12 in order to hold the cover 38 in place on the therapeutic device 10. Lenses 382 protrude through openings 383 formed in the cover 38 in order to accommodate light beams output from the lasers 20 and the light emitting diodes 22. The lenses 382 are formed of a clear molded silicone and form an integral unit stretching from one side of the cover 38 to the other. Disposed within each of the lenses 382 are fiber optic light guides 385, which are preferably formed of a low resolution glass image conduit, are used to conduct the light from the laser surface to the protruding portion of the lens 382 which rests against a patient's skin. In the preferred embodiment which uses VCSELs as the laser beam source, the guides 385 would be unnecessary due to the self-focusing (i.e., self-collimating) nature of the VCSELs. The fiber optic light guides, or rods, 385 are ground to be flat on one end which abuts the diode and are rounded at the opposite end as shown in FIG. 3C. The guides 385 are sized to be flush with a lower surface of the lens 382.

The lens structure 382 is co-molded with the silicone cover 38, forming a sealed barrier between the external surface of the instrument which contacts the patient's body and the face of the instrument 10. A suitable silicone adhesive, epoxy or other suitable bonding agent may be also be used to accomplish the mating of the cover 38 with the lens structure 382.

Support feet 384 are formed in the cover 38 to space the instrument from the patient's body so as to provide a more comfortable fit for the device 10 when being worn by the wearer. The feet 384, which extend outward from the face of the instrument, may be sized slightly larger than the lenses 382 so that the patient does not feel an uncomfortable sensation from lenses 382 pressing against the body.

FIG. 3B shows an alternative embodiment in which a plurality of glass or clear silicone optical windows 388 are provided to accommodate the light from the lasers 20 and the light emitting diodes 22. Relief areas 386 are formed in an outer surface of the cover 38 to accommodate the positions of the lasers and light emitting diodes on the therapeutic device 10. The flat lens is also preferably formed of the same clear silicone material as lens structure 382, due in part to the desired inherent flexibility of the silicone material. However, other suitable materials such as plastic or glass may be used in place of the clear silicone.

FIG. 3C illustrates additional details of the silicone cover 38 shown in FIG. 3A. More particularly, as can be seen in FIG. 3C, lenses 382 are formed so as to provide a one millimeter thick optically clear silicone lens which houses the fiber optic guide 385 at a point at which a laser beam or beam of light from an LED will exit lenses 382. The side walls of the lenses 382 are formed of a three millimeter thick silicone material to provide sufficient structural rigidity to support the lenses 382 when in position on a patient's body and pressure is being applied thereto.

The entire structure of the laser treatment device discussed above could be similar in size to a so-called "walkman" or portable radio. It is light-weight yet durable, with the silicone material providing a level of moisture resistance. Further, the structure of the device, with the exception of the semi-conductor components (i.e., the lasers, LEDs and the programmable controller), is flexible enough to conform to the contours of the patient's body.

In operation, the laser therapeutic device 10 is affixed to a patient by a physician or ancillary medical personnel using the strap 16 such that the housing 12, with silicone cover 38 in place, is positioned over the desired treatment location. The strap 16 is sterilized, disposable and may be made of nylon or a stretchable material to allow the therapeutic device 10 to be strapped about the patient's body and apply a positive biasing force to hold the therapeutic device 10 on a desired location on the patient's body. The strap may be provided with a velcro fastener or other suitable fastening device to adjustably secure it about the patient's body.

The operation of the therapeutic device 10 is initiated by operation of the switch 15. The hyper-red LEDs can provide a visible feedback (e.g., flashing once) to the user to confirm that the device is operational. Preferably, in use the switch 15 is covered by the silicone cover 38 so that the patient will not inadvertently turn the device off. The doctor or ancillary medical personnel operates the switch 15 prior to installing the sterilized silicone cover 38 about the housing 12. After the switch 15 is operated, the device 10 is applied to the desired area on the patient's body and the laser therapy begins.

The programmable controller 30, is preferably a low-power consumption device which, as discussed, is capable of approximately one-week of operation from a single battery charge. Therapeutic devices 10 having different treatment regimens programmed therein could be provided, with the physician selecting a particular device in accordance with an appropriate regimen depending on the patient's condition. Alternatively, the controller 30 may be provided with a PCMCIA port which interfaces with a so-called "smart card" or master programming card which can be inserted therein and a treatment regimen may be downloaded to the controller 30 by the treating physician. Alternatively, a serial interface to connect the device to a personal computer or similar device may be provided.

In a preferred embodiment of the present invention, a time period can be provided between the operation of the switch 15 and the actual initiation of the laser treatment regimen to allow sufficient time for the therapeutic device 10 to be properly positioned on the patient's body prior to initiation of the laser therapy. In an alternative embodiment, the switch 15 could be a pressure switch which is activated by the placement of the silicone cover 38 on the housing 12. By placing the silicone casing about the housing 12, the pressure switch 15 would be activated, thereby initiating the laser treatment regimen.

After being located on the patient's body, the patient simply wears the device for the prescribed period of time and is free to conduct themselves in the normal course. The device automatically delivers the prescribed laser therapy as determined by the programmable controller 30 while the patient goes about their normal routine.

In this fashion, a single doctor visit replaces the time consuming, and costly, multiple office visits required with prior art laser treatment regimens. With the present invention, a physician could initiate a laser treatment regimen using the therapeutic device 10 and allow the patient to leave with the device attached to their body for one week of laser therapy without the need for the patient to return to the physician's office. An appointment could be scheduled one week later for the physician to determine the success of the laser therapy. Further, since the therapeutic device 10 provides precisely timed and delivered laser treatments, the efficiency of the laser treatment is optimized. The result is a decrease in the overall length of the required treatment.

A clear advantage of treatment using the laser therapeutic device 10, is the freedom provided to the patient. For example, depending upon the nature of the prescribed laser therapy, the patient may only need to wear the therapeutic device 10 during certain hours of the day (e.g., while sleeping). In order to ensure that the patient properly positions the therapeutic device 10 on the body, the physician could outline the proper location on the body with a waterproof marking pen. The patient will not be permanently marked using such a pen, since the body will naturally eliminate the marks over the course of one to two weeks. In the interim, the patient will be provided with a clearly visible indicator as to the appropriate location of the therapeutic device 10 on the body, enabling the patient to remove the device 10 for purposes of bathing, etc.

Figure 4:
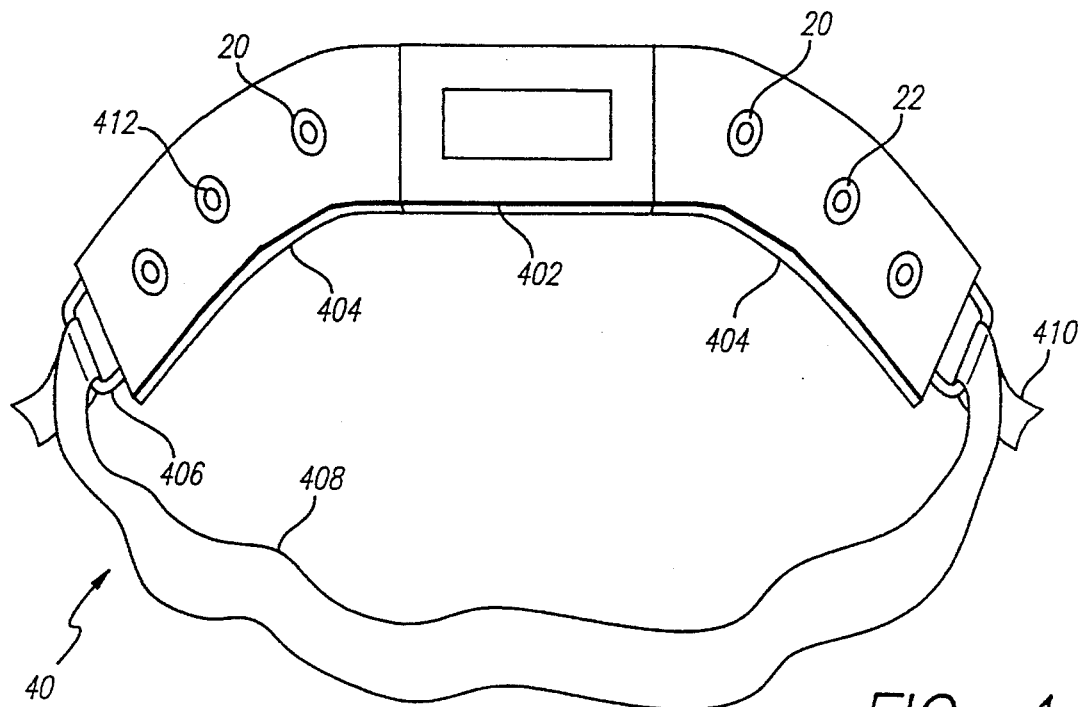
FIG. 4 is a plan view of a second embodiment of a laser therapeutic apparatus in accordance with the present invention.

FIGS. 4 and 4A–4C illustrate a second preferred embodiment of the laser therapeutic device 40 in accordance with the present invention. The embodiment shown in FIG. 4 provides a laser bandage suitable for use on a patient's knee, elbow, shoulder or other joint area. A power supply and control circuit 402 is identical to that discussed above in conjunction with the first preferred embodiment. The power supply and control circuit 402 has bonded thereto a pair of flexible silicone wing structures 404 in which are disposed lasers 20 and, if desired, hyper-red LEDs 22. The lasers and LEDs 20, 22, respectively, are sandwiched between silicone layers in the same fashion as described above. The flexible silicone wing structure is bonded to the housing of the power supply and control circuit 402. Flexible flat wire connectors are used to connect the lasers and light emitting diodes with the power supply and control circuit. The silicone wing structures 404 are provided with relieved areas 412 which allow a lens or window structure similar to that shown in FIGS. 3A–3C to conduct light from the lasers and LEDs 20, 22 to the patient's body. The relieved areas 412 also provide a spacing between the lasers and LEDs and the patient's body. The wing structures 404 are provided with hooks 406 for receiving therein a strap 408. The strap 408 may be permanently bonded to the hooks 406 or may be provided with a velcro fastening material to allow for a custom fit of the therapeutic device 40 on various areas of the patient's body.

Figure 4A:
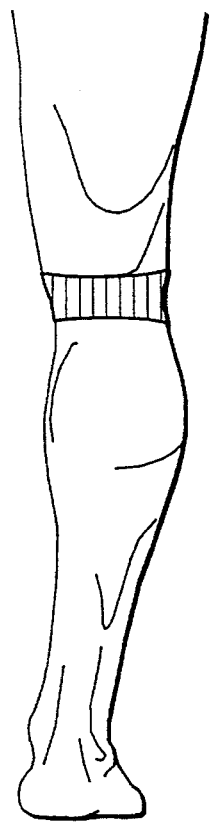
FIGS. 4A, 4B, and 4C illustrate back, side and front views of a possible application of the laser therapeutic apparatus shown in FIG. 4.
Figure 4B:
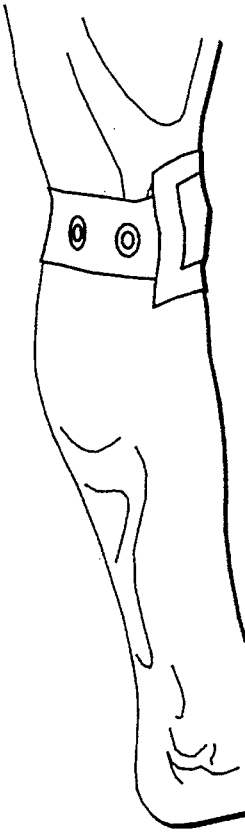
Figure 4C:
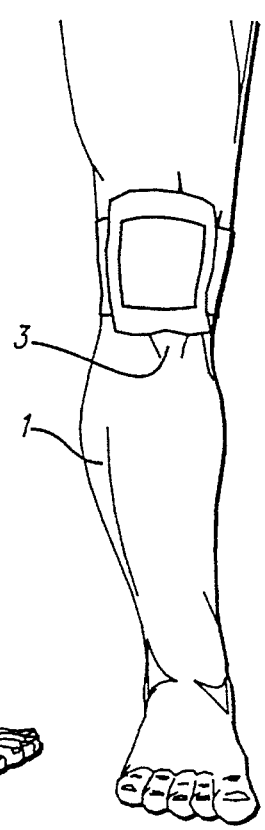

In particular, as can be seen in FIGS. 4A–4C, the device shown in FIG. 4 is suitable for use on a patient's knee. The strap 408 can fit about the leg 1 of a wearer and the power supply and control circuit 402 would be positioned adjacent the knee 3. The lasers and the hyper-red LEDs would extend about the side circumference of the knee 3 and provide for laser therapy to both sides of a patient's knee. While the embodiment shown in FIG. 4 uses lasers and LEDs on both sides of the power supply and control circuit 402, such a bandage may be provided with lasers and/or LEDs on only one side of the power supply and control circuit 402 in order to provide localized treatment of a particular injury.

Figure 5:
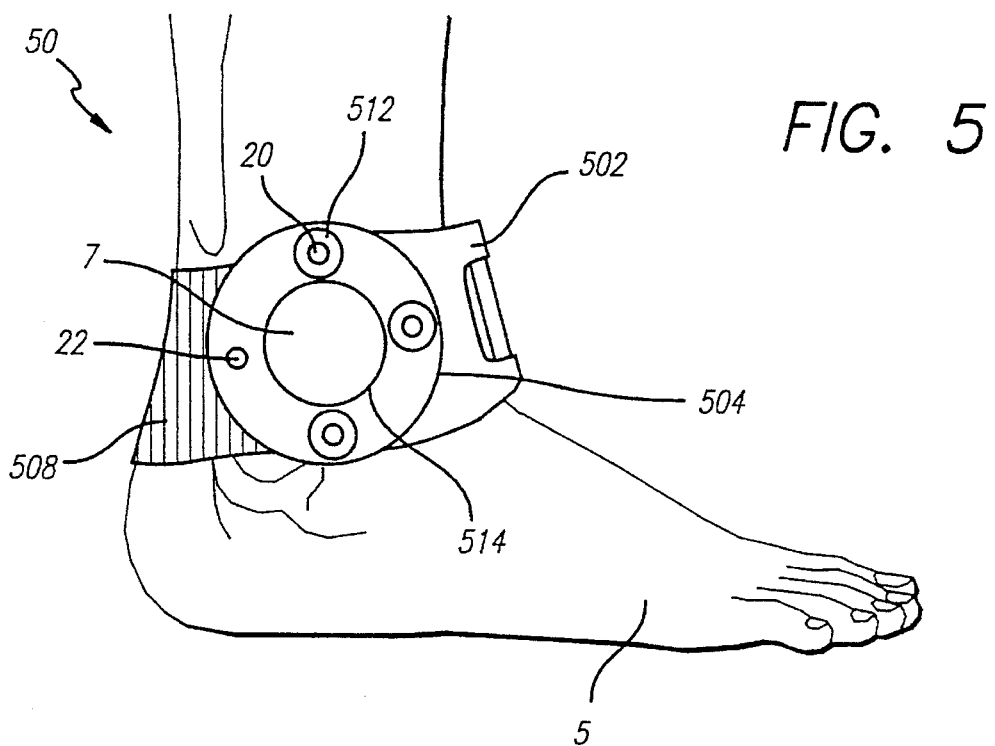
FIG. 5 is side view a third embodiment of a laser therapeutic apparatus in accordance with the present invention.
Figure 5A:
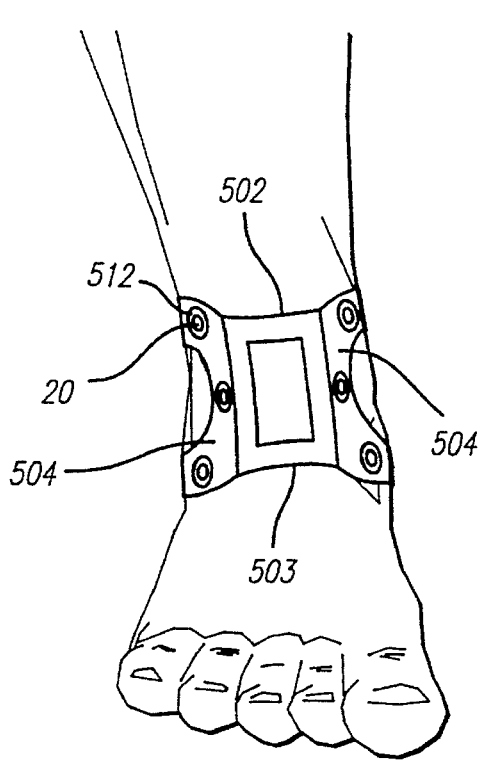
FIGS. 5A and 5B are front and rear views, respectively, of the laser therapeutic apparatus shown in FIG. 5 as applied to the ankle of a patient undergoing laser therapy.
Figure 5B:
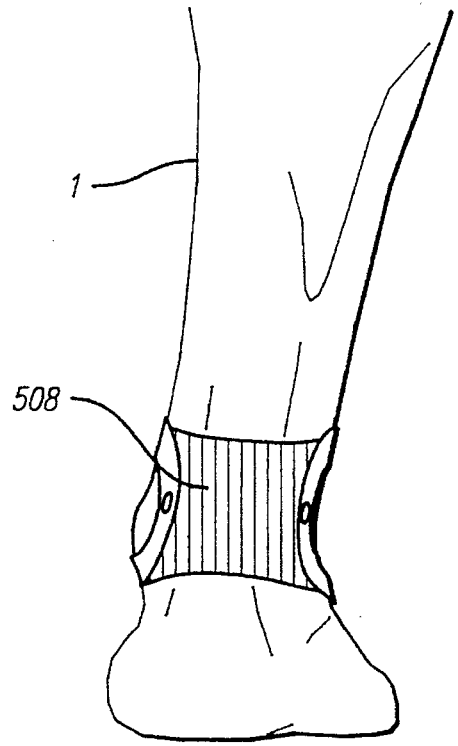

FIGS. 5, 5A and 5B illustrate a third preferred embodiment of a laser therapeutic device 50 in accordance with the present invention. As with the first and second embodiments, the third embodiment includes a strap 508 for supporting the therapeutic device 50 on a patient's body. The device shown in FIG. 5 is specifically designed as an ankle bandage for use in providing laser therapy to the ankle area of a patient. Lasers 20 and a hyper-red LED 22 are mounted on a flexible, silicone donut-shaped structure 504 which includes a removed portion 514 to accommodate the ankles 7 of a patient. A power supply and control circuit 502 is provided as seen in more detail in FIG. 5A.

The silicone structure 504 can be bonded to the power supply and control circuit 502 as in the second embodiment discussed above, and provide simultaneous treatment to both sides of a patient's ankle. The power supply and control circuit 502, which includes a housing formed in the same manner as that in the first embodiment, formed to include an arc-shaped portion 503 which accommodates the in-step of the wearer's foot 5. The strap 508 for supporting the therapeutic device 50 of the third embodiment is preferably elastic in nature so as to be able to be slipped over the foot of the patient and positioned in the appropriate location on the patient's ankle. An elastic/velcro strap could be provided to afford the patient with the optimum range of adjustability.

Figure 6:
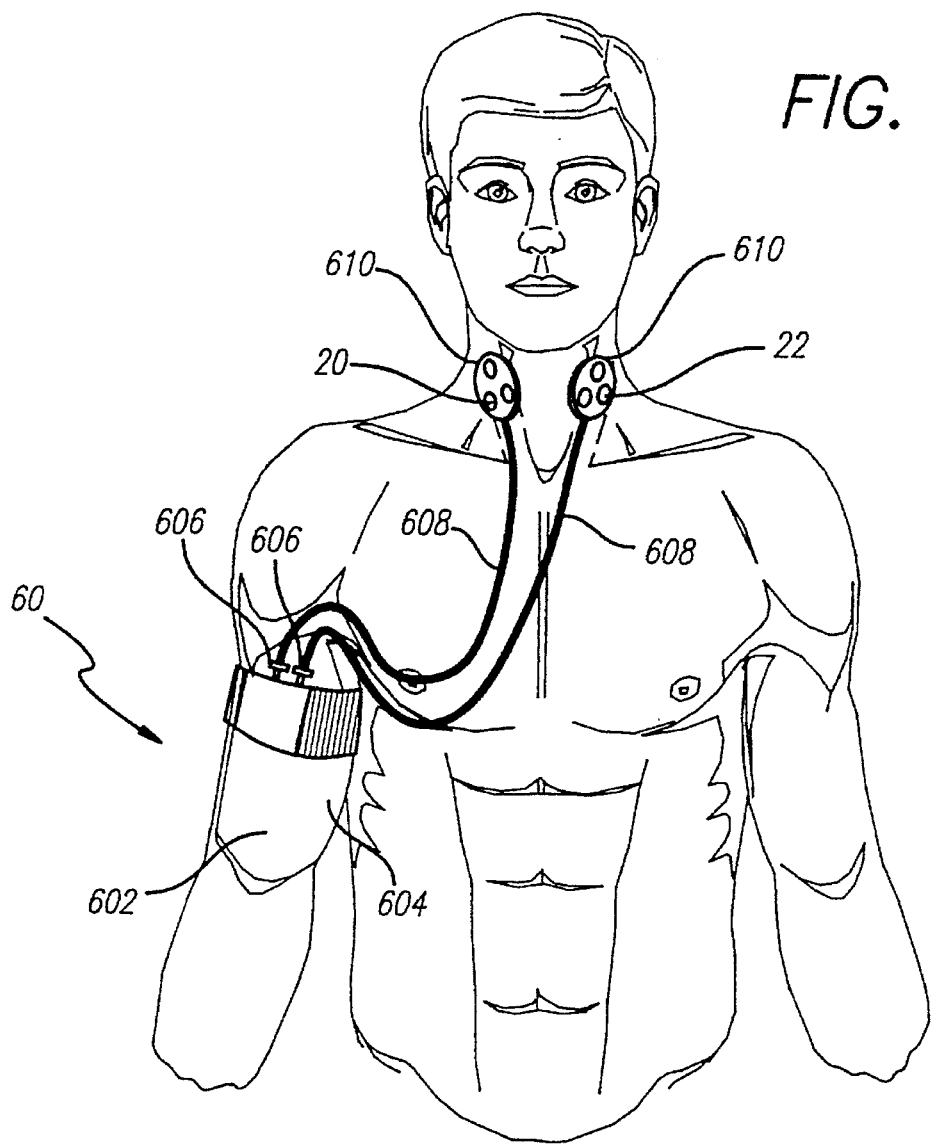
FIG. 6 illustrates a fourth embodiment of a laser therapeutic apparatus in accordance with the present invention.

FIG. 6 illustrates a fourth preferred embodiment of a laser therapeutic device 60 in accordance with the present invention. In the fourth embodiment, the therapeutic device 60 may be worn by the wearer on a convenient location such as the arm shown in FIG. 6. The therapeutic device, which is similar in structure to that shown in FIG. 4, includes a power supply and control circuit 602 having attached thereto a strap 604 for retaining the power supply and control circuit 602 in the desired position on the wearer's body.

A pair of electrical contacts 606 engage the power supply and control circuit 602 and provide power to a pair of diode treating pads 610 which are preferably three-inch circular pads (but can be various sizes and shapes depending on the specific application) having a plurality of lasers and/or hyper-red LEDs 20, 22 disposed therein in a "sandwich" structure similar to the embodiments discussed above.

The circuit for controlling the lasers provided on the pads is the same as that shown in FIG. 1A. The only modification would be the length of the wires connecting the current regulators to the lasers. In this case, such wires would be long enough to allow the wearer to position the pads 610 in a desired location.

The pads 610 may be made of co-molded silicone or other flexible polymer material and are provided with a lens structure or optical windows as with the housing and cover of the first embodiment shown in detail in FIGS. 3A–3C. The cover would be presterilized and disposable to prevent cross-contamination and maintain sterility. In addition, the cover includes an adhesive backing which allows the pads 610 to be adhered to the desired location of the patient's body.

The pads 610 connect with the electrical connectors 608 to receive power from the power supply and control circuit 602. The electrical connectors 608, which are preferably copper or aluminum, are shielded in a electrically insulated material such as plastic, in a known manner similar to that used for stereo headphones.

In this embodiment, it is unnecessary to constantly remove and re-position the power supply and control circuit 602. Instead, the power supply and control circuit 602 is positioned on the patient's body in a convenient location which is most comfortable for the patient. Then, the diode treating pads 610 are located on the area of the body requiring laser therapy, and may be affixed thereto using a suitable adhesive. The pads 610 are provided with a disposable, pre-sterilized cover having a plurality of lenses and feet formed thereon as shown in FIGS. 3A–3C. The adhesive would preferably be applied to the feet of the cover to avoid possible attenuation of the beam. The plugs 606 are then connected with the power supply and control circuit 602 to energize the lasers in accordance with the treatment regimen stored in the power supply and control circuit 602.

Figure 7:
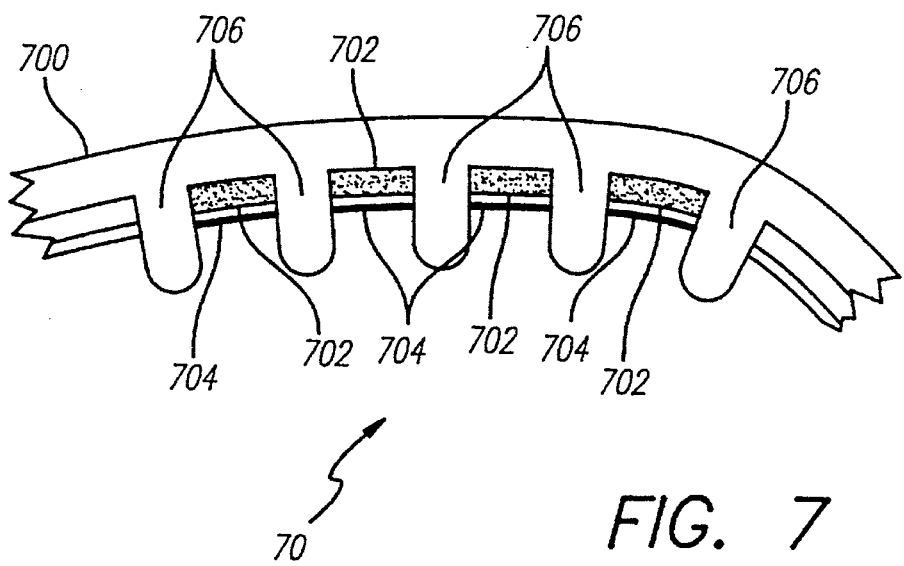
FIG. 7 illustrates a partial side view of a fifth embodiment of a laser therapeutic apparatus in accordance with the present invention.

FIG. 7 illustrates a partial side cross-sectional view of a fifth preferred embodiment of the laser therapeutic device 70 suitable for use in treating a patient's scalp. As can be seen in FIG. 7, a silicone outer casing 700 has disposed therein a plurality of lasers 702. A plurality of co-molded clear silicone windows 704 are disposed over the lasers 702 and are bonded with the silicone outer casing 700. This bandage, which has an overall thickness of +/–3 millimeters, is flexible to accommodate the particular needs of both the doctor and the patient undergoing laser therapy. In addition, molded silicone feet 706 are provided to support the bandage against a patient's body. In the embodiment shown in FIG. 7, the hyper-red LEDs will be connected with a power supply and control circuit such as that shown in embodiments 1–4 discussed above.

FIG. 8 shows a sixth preferred embodiment of a laser therapeutic device 80 in accordance with the present invention. As can be seen in FIG. 8, a silicone pad 800 is used to encompass a plurality of hyper-red LEDs and lasers 802. The silicone casing 800 is provided with molded light channels 804 which allow the light produced by the LEDs and lasers to pass therethrough. As with the embodiments of the silicone casing shown in FIG. 3, this embodiment of the silicone casing 800 may be provided with a plurality of spacing support feet 806 which are used to position the therapeutic device 80 at the optimum distance from the wearer's body. Each of the hyper-red LEDs or lasers 802 would be connected with a power supply and control circuit such as that discussed above in conjunction with FIG. 1–7.

In FIG. 8, a power supply lead 808 would be used to provide power from the power supply and control circuit which may be identical to that used in the above embodiments. Finally, the embodiment of FIG. 8 may be provided with optional lens structures 810 which would be formed of a co-molded clear silicone which would then be positioned within the silicone casing 800 to protect the lasers and hyper-red LEDs disposed therein as well as serving to prevent the spread of bacteria.

FIGS. 9A–9C illustrate a seventh preferred embodiment of the laser therapeutic device 90 in accordance with the present invention. In this embodiment, the wearer would wear the therapeutic device 90 on the hand 9, or more specifically about the wrist 11. A wristband 900 is provided to maintain the position of the therapeutic device 90. A power supply and control circuit 902 is provided such as that shown in embodiments 1–6 discussed above. A laser diode and LED pad would be provided adjacent to power supply and control circuit 902 to provide the laser beam and light energy from the lasers and LEDs to the patient. This embodiment of the present invention would be useful in treating carpal tunnel syndrome. The lasers 20 and the hyper-red LED 22 would be the same as those used in embodiments 1–6 discussed above. As with the first embodiment, a heat sink 36 is illustrated in FIG. 9A in association with a laser diode 20 but would not be required with a VCSEL.

As can be seen in more detail in FIG. 9A, a silicone pad 904 is provided as the outer casing for the therapeutic device 90. Bonded to the silicone pad 904 is a flexible circuit board 910 having mounted thereon the lasers and LEDs 20, 22. Bonded to the flexible circuit board 910 is a clear, co-molded silicone cover 906 which serves as a lens 908 for the laser diode and hyper-red LEDs 20, 22.

The silicone pad 904 may be formed of a thickness of silicone material ranging from 1 to 3 millimeters. The flexible circuit board is generally on the order of 1 millimeter in thickness and the co-molded, clear silicone cover 906 may vary in thickness from 1 to 3 millimeters adjacent the flexible circuit board 910 to 1 millimeter at the lens apex 908, producing a device having an overall thickness on the order of 3 to 6 millimeters. The light produced by the lasers 20 and the hyper-red LED 22 passes through the clear, co-molded silicone structure without substantive attenuation of the power of the light beam.

FIGS. 10–13 illustrate the eighth through eleventh preferred embodiments of a laser therapeutic device in accordance with the present invention. Such FIGURES illustrate various alternative embodiments for the structure of the treatment bandage or strip that is applied to the body. However, the control circuit for use with these embodiments is the same as that shown in FIG. 1A. While the control circuit is not illustrated, the connections of the control circuit to the embodiments shown in FIGS. 10–13 would be in the same manner as the embodiment of the present invention shown in FIG. 6 in which the remote pads 610 are provided with wires to connect with the power supply and control circuit.

In the eighth preferred embodiment shown in FIG. 10, a glove-like structure, preferably formed of a co-molded silicone material such as that used in the embodiment shown in FIG. 9A has mounted thereon an array of lasers and/or hyper-red LEDs 20, 22 to provide for laser therapy over the entire hand portion of a patient undergoing treatment. The lasers and/or LEDs are preferably spaced approximately every ½ inch. The power supply and control circuit could be worn by the patient undergoing treatment on a convenient location on the patient's body such as the upper arm. Wire connectors 104 would then be provided from the glove-like structure 102 to the power supply and control circuit to provide the necessary power to energize the lasers 20 and the light emitting diodes 22. However, the programmable controller would be the same as that in the previously discussed embodiments.

Figure 11:
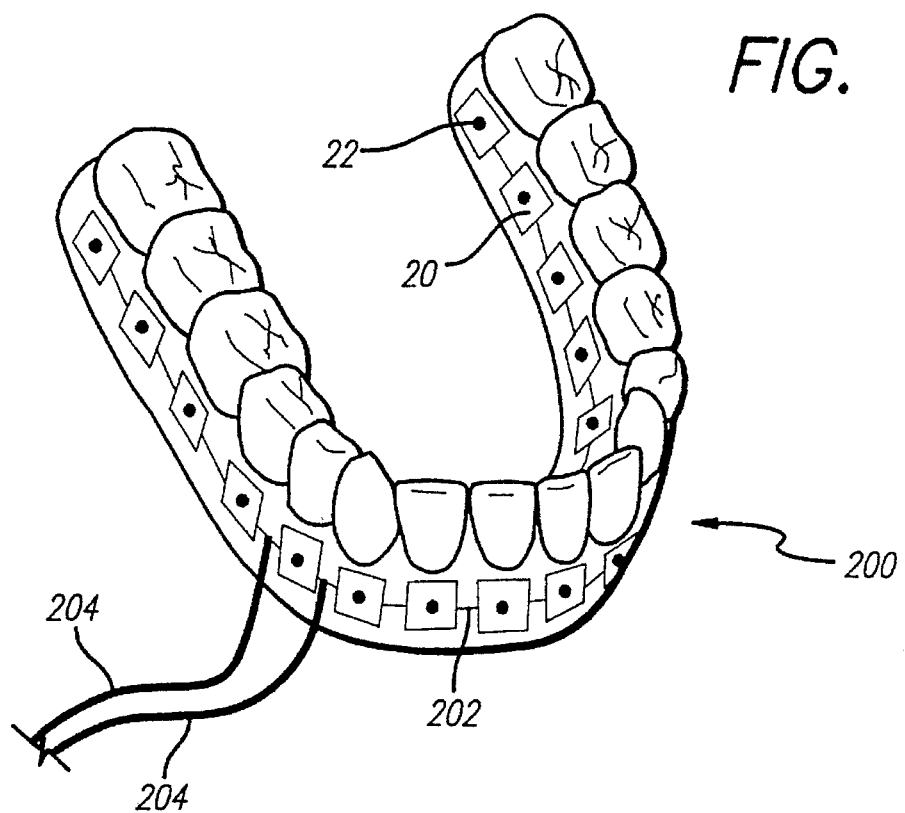
FIG. 11 illustrates a ninth embodiment of a laser therapeutic apparatus in accordance with the present invention.

The ninth preferred embodiment of the present invention shown in FIG. 11 includes a laser therapeutic device 200 specifically for treating oral medical conditions, and in particular periodontal conditions. The device 200 includes a silicone structure 202 and a plurality of lasers and/or hyper-red LEDs 20, 22 disposed about the surface of the silicone support 202 along the gingival margin area. The silicone structure 202 would be formed in the manner shown in FIGS. 7 and 9, and would be resistant to moisture penetration. The lasers would be positioned at the gum margin, and could be provided either as a continuous ribbon of lasers (VCSELs), or a series of individual VCSELs as illustrated. The therapeutic device 200 will typically include a pair of insulated leads 204 for connecting the device 200 to an external power supply and control circuit which could be held by the patient, or, alternatively could be worn by the patient in the manner shown in FIG. 6. The leads would be insulated to prevent any possible leakage of power from the power supply or the lasers 20 and hyper-red LEDs 22.

Figure 12:
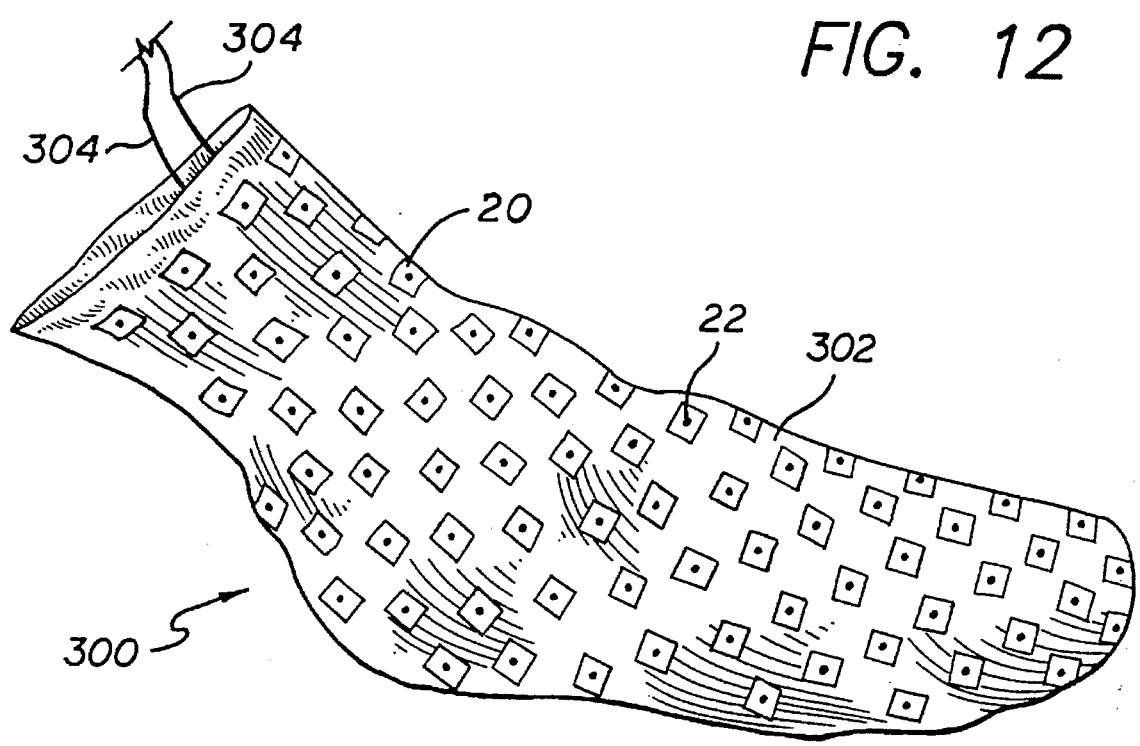
FIG. 12 illustrates a tenth embodiment of a laser therapeutic apparatus in accordance with the present invention.

The tenth preferred embodiment of the present invention shown in FIG. 12 provides for a sock 302 made of silicone or other suitable material which is includes a plurality of lasers 20 and/or hyper-red LEDs 22. This embodiment is formed in a manner identical to the glove structure 102 shown in FIG. 10 and would be connected with a remote power supply and control circuit via leads 304.

Figure 13:
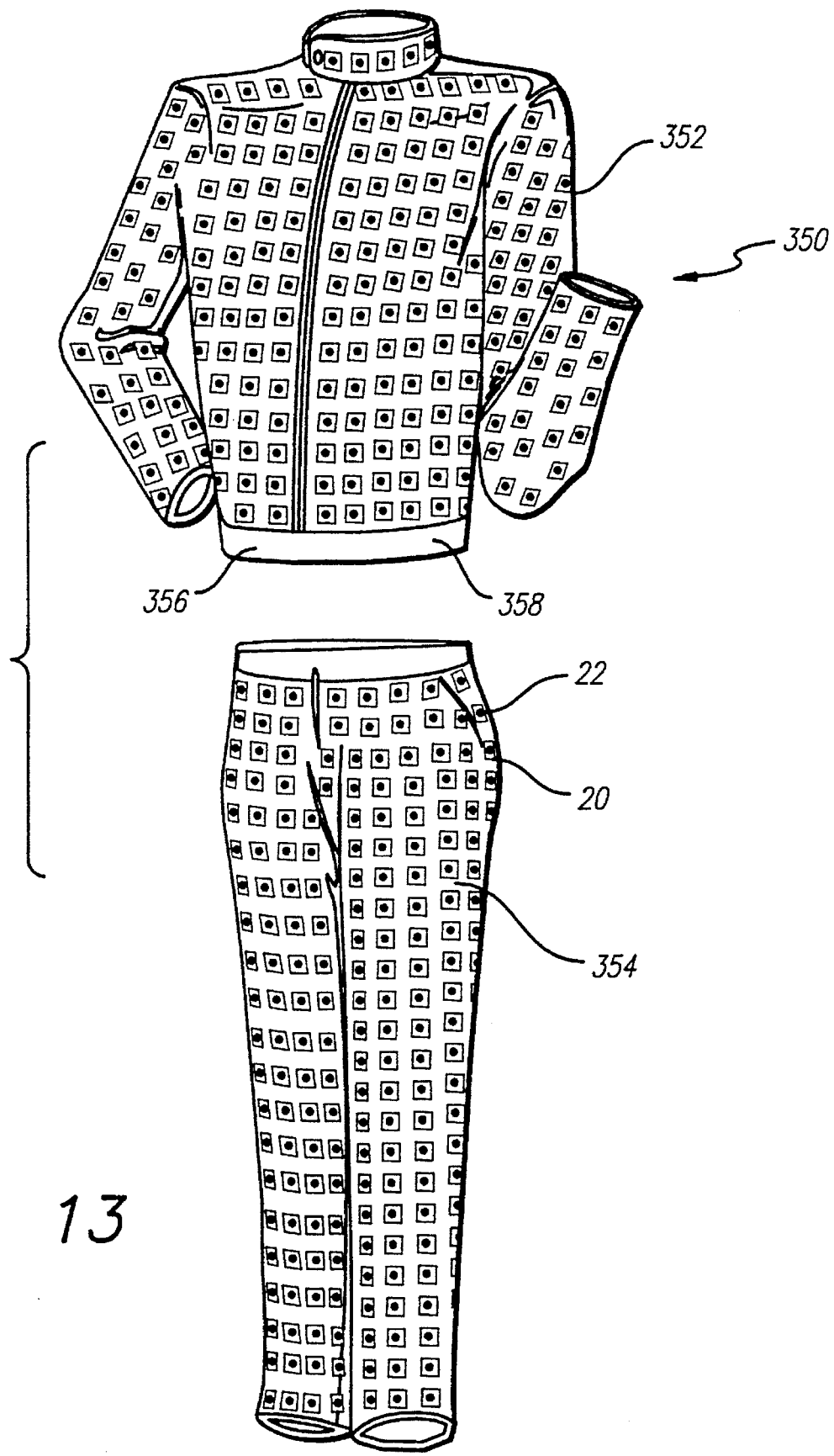
FIG. 13 illustrates an eleventh embodiment of a laser therapeutic apparatus in accordance with the present invention.

The eleventh preferred embodiment of the present invention shown in FIG. 13 includes a two-piece treatment suit to be worn by a patient to enable full body laser therapy using low power laser beam energy. This embodiment, which would typically be utilized in a hospital setting, includes a top jersey 352 and a bottom pants structure 354. The jersey 52 and pants 54 can be provided with areas 56 and 58, respectively which do not incorporate lasers and/or hyper-red LEDs in suitable positions. As with the embodiment of the present invention shown in FIGS. 10–12, this embodiment of the present invention would typically require an external power supply having sufficient output power to supply the plurality of lasers and/or light emitting diodes. In addition, although not illustrated, the jersey 52 and pants 54 could be provided with fastening mechanisms such as velcro or a zipper along an entire length thereof to enable the device to be easily placed on the patient While the above disclosure is of the currently preferred embodiments of the present invention, the invention is in no way limited to the specific embodiments discussed. For example, additional devices may be formed of silicone or other suitable material to treat specific body parts such as a patient's nose, ears, etc. Materials other than silicone may be used to form the devices of the present invention such as rubber, polyurethane, or molded ethylene vinyl acetate (EVA).

Further, the apparatus of the present invention may be provided with an interface port to be connected to a personal computer to enable the physician to download data such as a treatment regimen to the programmable controller. Alternatively, the physician may be able to download different power and/or wavelength parameters to generate different laser beams having such characteristics.

Additionally, it may be possible to incorporate heart rate, blood pressure, or blood chemistry sensors as they become available, and temperature sensors on the device to monitor the patients vital statistics during the course of the treatment regimen. These statistics could be stored by the programmable controller and retrieved by the attending physician at the end of the treatment regimen.

The present invention is also applicable for use in photo dynamic therapy (PDT). In essence, PDT is the process of injecting photosensitive chemicals or compounds into the blood stream of a patient. The photosensitive chemicals or compounds are selectively absorbed by cancer cells. By irradiating the afflicted area of the patient's body with specific wavelength laser beam energy, the cancer cells which have absorbed the photosensitive chemicals or compounds are destroyed. Using the present invention, a sheet or bandage may be used to treat superficial cancers by applying lasers (VCSELs) that are wavelength specific for PDT combined with lasers (VCSELs) that are wavelength specific for stimulating the body's immune system.

In addition, for skin grafts and transplants, the structure of the present invention could be used in sheet form to stimulate the growth of layers of skin cells, collagen cells, or bone cells grown in the laboratory as well as direct application of the sheet or bandage to the area on the body where newly generated tissue is placed to enhance the success rate of the transplanted tissue.

It is intended that all such modifications and/or additions be encompassed within the scope of the present invention. The invention is solely limited by the claims which appear below.

I claim:

1. A laser therapeutic device for treating a patient comprising:
   a flexible bandage;
   a power supply, disposed on said flexible bandage;
   at least one laser diode disposed in said flexible bandage and operatively connected with said power supply, for generating a laser beam;
   programmable control means, operatively connected with said power supply and said at least one laser diode, for selectively enabling said at least one laser diode for a predetermined period of time at a plurality of programmed intervals, said programmable control means including means for storing a treatment regimen for said laser therapeutic device; and
   attachment means, connected with said flexible bandage, for attaching said laser therapeutic device to the patient to provide the patient with a laser treatment in accordance with the stored treatment regimen.

2. The laser therapeutic device of claim 1, wherein said flexible bandage comprises a sheet of flexible silicone material having a predetermined size, wherein said at least one laser diode, said power supply, and said programmable control means are disposed in said silicone material.

3. The laser therapeutic device of claim 2, wherein said power supply comprises a battery.

4. The laser therapeutic device of claim 2, wherein said programmable control means includes programmable timing means for measuring a first predetermined period of time, and laser enabling means, responsive to said programmable timing means, for enabling said laser diode after said first predetermined period of time.

5. The laser therapeutic device of claim 4, wherein said programmable timing means measures a second predetermined period of time after said first predetermined period of time, said laser enabling means being responsive to said programmable timing means for disabling said laser diode after said second predetermined period of time.

6. The laser therapeutic device of claim 1, wherein said flexible bandage is formed of co-molded silicone, said programmable control means including a flexible circuit board having mounted thereon said programmable control means.

7. The laser therapeutic device of claim 6, wherein said power supply comprises a flexible lithium polymer battery operatively connected with said flexible circuit board for supplying power thereto.

8. The laser therapeutic device of claim 7, wherein said co-molded silicone forms a housing for said flexible circuit board and said battery.

9. The laser therapeutic device of claim 8, further including a plurality of laser diodes imbedded in said co-molded silicone, each of said laser diodes being operatively connected with said programmable control means and operable for generating a laser beam to be applied to the desired location on the patient's body.

10. The lseer therapeutic device of claim 1, further comprising at least one remote flexible bandage having disposed therein at least one laser diode for generating a laser beam to be applied to the patient, the remote flexible bandage being operatively connected to the power supply and peogrammable control means and being affixable to the patient's body at a second location remote from the first location.

11. The laser therapeutic device of claim 1, wherein said at least one laser diode comprises a vertical cavity surface emitting laser diode.

12. The laser therapeutic device of claim 1, wherein said flexible bandage is formed of a flexibly resilient material, said programmable control means including a flexible circuit board having mounted thereon logic circuit means for controlling operation of said at least one laser diode.

13. The laser therapeutic device of claim 12, wherein said power supply comprises a flexible lithium polymer battery operatively connected with said flexible circuit board for supplying power thereto.

14. The laser therapeutic device of claim 13, wherein said flexibly resilient material forms a housing for said flexible circuit board and said battery.

15. The laser therapeutic device of claim 14, further including a plurality of laser diodes imbedded in said flexibly resilient material, each of said laser diodes being operatively connected with said logic circuit means and operable for generating a laser beam to be applied to the desired location on the patient's body.

16. The laser therapeutic device of claim 12, wherein said flexibly resilient material comprises silicone.

17. The laser therapeutic device of claim 12, wherein at least a portion of said flexible bandage is formed of optically clear silicone.

18. A laser therapeutic device for treating a patient comprising:
   a flexible bandage formed of co-molded silicone;
   means for attaching said flexible bandage to a first location on the patient's body;
   a battery power supply, connected with said flexible bandage;
   a plurality of laser diodes disposed in said flexible bandage and operatively connected with said power supply, for generating a laser beam;
   programmable control means, operatively connected with said power supply and said at least one laser diode, for selectively enabling said at least one laser diode for a predetermined period of time at a plurality of predetermined intervals, said flexible bandage including a flexible circuit board having said programmable control means mounted thereon and said co-molded silicone forming a housing for said flexible circuit board and said battery; and
   a removable cover formed of a resilient material and adapted to fit about said housing, said cover having formed therein a lens for each of said plurality of laser diodes.

19. The laser therapeutic device according to claim 10, wherein said cover is formed of co-molded silicone and includes a plurality of openings formed therein for receiving said lenses for each of said plurality of laser diodes.

20. The laser therapeutic device according to claim 19, wherein said lenses are formed of optically clear silicone and protrude from a first side of said cover through to a second side of said cover.

21. The laser therapeutic device of claim 20, wherein said lenses are integrally formed from a sheet of said optically clear silicone, each of said lenses having disposed therein an optical guide for conducting light from said plurality of laser diodes.

22. The laser therapeutic device of claim 21, wherein each of said optical guides is formed of a low resolution glass image conduit and is sized so as to be flush with a bottom surfaces of said lens.

23. A laser therapy treatment method for treating a patient with laser energy, the method comprising the steps of:

disposing at least one laser diode in a flexible bandage;

connecting a power supply with said flexible bandage;

operatively connecting said at least one laser diode with said power supply;

attaching said flexible bandage and said power supply to the patient's body;

providing a treatment storage device for storing a treatment regimen for said laser therapeutic device; and providing a programmable controller fox selectively enabling said at least one laser diode for a predetermined period of time at a plurality of predetermined intervals in accordance with the stored treatment regimen.

24. The method according to claim 23, further including the step of forming said flexible bandage from co-molded silicone, said flexible bandage being formed so as to contain said at least one laser diode and said power supply therein.

25. The method according to claim 23, wherein the step of selectively enabling includes the steps of:

measuring a first predetermined period of time; and enabling said at least one laser diode after said first predetermined period of time.

26. The method according to claim 25, further including the steps of:

measuring a second predetermined period of time after said first predetermined period of time; and disabling said at least one laser diode after said second predetermined period of time.

27. A laser therapeutic device for treating a patient comprising:

a flexible bandage;

means for attaching said flexible bandage to a first location on the patient's body;

a power supply, connected with said flexible bandage;

means for attaching said flexible bandage and said power supply to the patient's body;

light source means, coupled with said flexible bandage and including at least one of a source of laser light and a hyper-luminescent light emitting diode, for generating at least one beam of light, said light source means being operatively connected with said power supply;

storage means for storing prescribed treatment regimen for treating the patient; and programmable control means, operatively connected with said power supply and said light source means, for selectively enabling said light source means for a predetermined period of time at a plurality of predetermined intervals in accordance with said stored prescribed treatment regiment.

28. The laser therapeutic device of claim 27, wherein said source of laser light comprises a vertical cavity surface emitting laser diode.

* * * * *

UNITED STATES PATENT AND TRADEMARK OFFICE
CERTIFICATE OF CORRECTION

PATENT NO : 5,616,140
DATED : April 1, 1997
INVENTOR(S): PRESCOTT, Marvin A.

It is certified that error appears in the above-identified patent and that said Letters Patent is hereby corrected as shown below:

Column 16, line 10,        Replace "lseer" with -- laser --.

Column 17, line 1,         Replace "claim 10" with -- claim 18 --.

Signed and Sealed this

Twenty-third Day of November, 1999

Attest:

Q. TODD DICKINSON

*Attesting Officer*    *Acting Commissioner of Patents and Trademarks*